United States Patent [19]
Li et al.

[11] Patent Number: 5,817,514
[45] Date of Patent: Oct. 6, 1998

[54] $O^6$-METHYLGUANINE-DNA-METHYLTRANSFERASE (MGMT) SPECIFIC ANTIBODIES

[75] Inventors: Benjamin Fuk Loi Li; Teck Choon Ayi, both of Singapore, Singapore

[73] Assignee: National University of Singapore, Singapore

[21] Appl. No.: 436,464

[22] PCT Filed: Nov. 29, 1993

[86] PCT No.: PCT/GB93/02449

§ 371 Date: Jun. 1, 1995

§ 102(e) Date: Jun. 1, 1995

[87] PCT Pub. No.: WO94/12660

PCT Pub. Date: Jun. 9, 1994

[30]    Foreign Application Priority Data

Nov. 27, 1992 [GB]  United Kingdom .................... 9224888

[51] Int. Cl.$^6$ .............................. C07K 16/40; C12N 5/12; G01N 33/577
[52] U.S. Cl. ........................... 435/338; 435/7.4; 435/7.6; 435/70.21; 435/172.2; 530/388.26; 530/391.1; 530/391.3
[58] Field of Search ............................ 530/388.26, 391.1, 530/391.3; 424/184.1; 435/7.1, 7.4, 7.6, 70.21, 172.2, 338

[56]    References Cited

U.S. PATENT DOCUMENTS 5,407,804  4/1995  Yarosh .

OTHER PUBLICATIONS

Ostrowski et al. Carcinogenesis (1991) 12, 1739–1744.
Ostrowski et al. Cancer Research (1991) 51, 3339–3344.
Von Wronski et al. J. Biol. Chem. (1991) 266, 1064–1070.
Brent et al. Cancer Research (1990) 50, 58–61.
Shiota et al. Biochemistry (1992) 31(7), 1897–1903.
Published International Application WO 93/24837 (publication date: Sep. 12, 1993); Category P,X.
Ayi et al. Cancer Research (1992) 52, 6423–6430; Category P,X.
Souliotis Carcinogenesis (1989) 10(7), 1203–1208 (corresponding abstract only enclosed as appended to the International Search Report) *2.
Tan et al. Biochemistry (1990) 39, 9234–9240.
Zarbl et al. Nature (1985) 315, 382–385 (p. 1).
Mitra et al. Proc. Natl. Acad. Sci. USA (1989) 86, 8650–8654 (p. 1).
P.D. Lawley Chemical Carcinogens vol. I., Ed. C.E. Searle ACS Monograph 182, American Chemical Society, Washington, 1984 (p. 2) *1.
Lindahl et al. Ann. Rev. Biochem. (1988) 57, 133 (p. 2) *2.
A.E. Pegg Cancer Research (1990) 50, 6119–6129 (p. 2).
Wronski et al. Cancer Communications (1989) (1) 5, 323–329 (p. 2).
Lee et al. Br. J. Cancer (1992) 66, 355–360 (p. 3).
Tano et al. Proc. Natl. Acad. Sci. USA (I 990) 87, 686–690 (p. II).
Studier et al. Methods Enzymol. (1990) 185, 60–88; copy of pages 60 and 61 only provided (p. 11).
Bhattacharyya et al. Nucleic Acids Res. (1988) 16, 6397–6410 (p. 12).
Harlow and Lane, Antibodies: A Laboratory Manual, Cold Spring Harbour N.Y. 1988 (p. 14); copy not provided.
Pegg et al. Carcinogenesis (London) (1991) 12, 1671–1677.
Li & Swann Biochemistry (1989) 28, 5779–5786.

*Primary Examiner*—Lila Feisee
*Assistant Examiner*—Nancy A. Johnson
*Attorney, Agent, or Firm*—Nixon & Vanderhye

[57]    ABSTRACT

The present invention provides antibodies capable of discriminating between native human MGMT and an active site alkylated form of this enzyme in an immunoprecipitation procedure.

Monoclonal antibodies having such discriminating ability are obtainable from hybridoma ECACC 92112510 and hybridoma ECACC 93112514, which were deposited at the European Collection of Animal Cell Cultures, UK under the Budapest Treaty on 25th Nov. 1992 and 25th Nov. 1993 respectively. The monoclonal antibody of hybridoma ECACC 92112510 has been designated Mab 5H7. The monoclonal antibody of hybridoma ECACC 93112514 has been designated Mab 3C7.

12 Claims, 7 Drawing Sheets

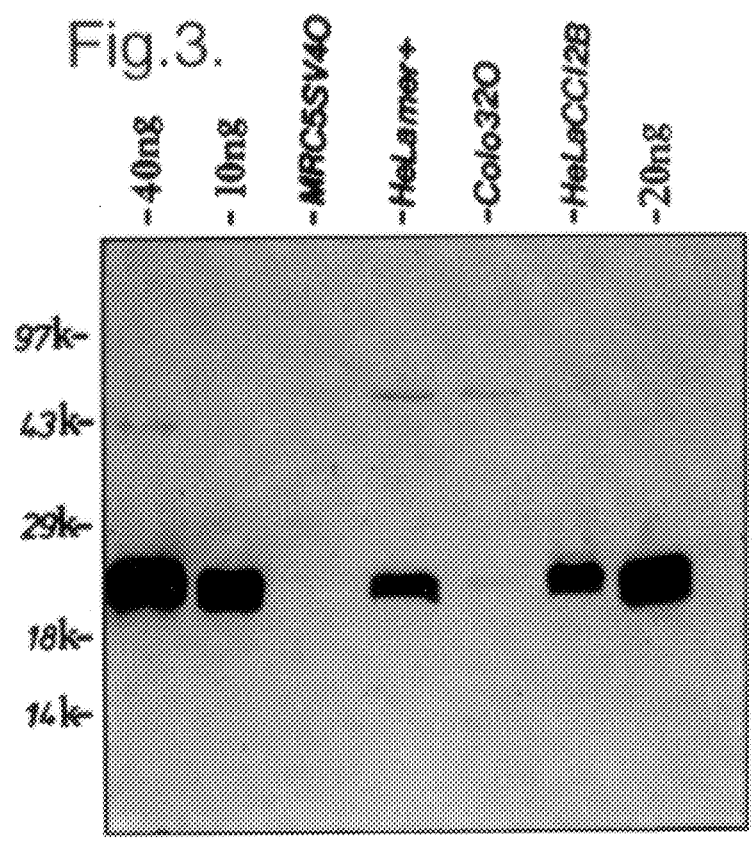
Fig. 3.
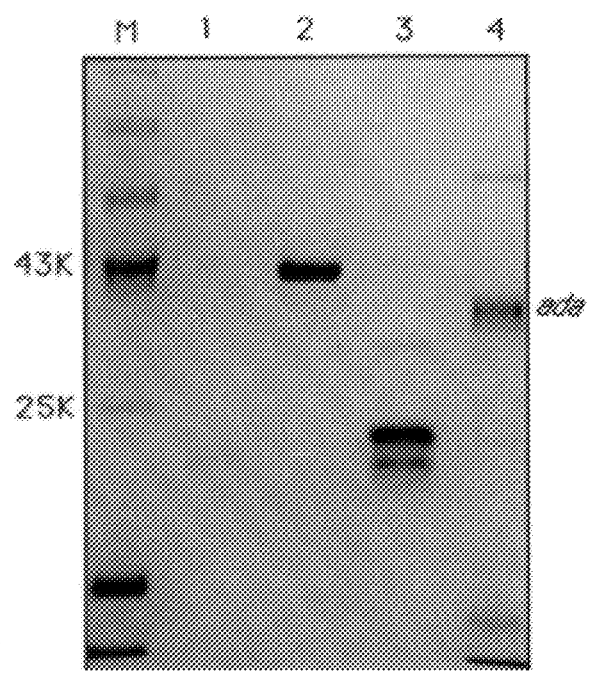
Fig. 4.
A. Coomassie Blue
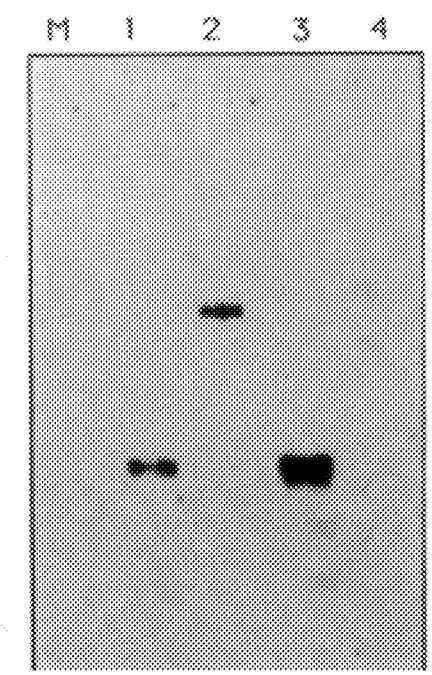
B. Western

HeLa-CC2B     HeLa-mer⁻     MRC5-SV40

DARK   SLIGHT   STRONG DARK     WEAK DARK     VERY WEAK

STRENGTH OF SIGNAL INDICATED
IN BOXES

DARK  WEAK DARK  WEAK  SLIGHT DARK  GOOD  STRONG

STRENGTH OF SIGNAL INDICATED IN BOXES

A.

22kd-

B.

22kd-

$O^6$-METHYLGUANINE-DNA-METHYLTRANSFERASE (MGMT) SPECIFIC ANTIBODIES

The present invention relates to monoclonal antibodies capable of preferentially binding one of human $O^6$-methylguanine-DNA-methyltransferase (MGMT) and active site alkylated derivatives thereof, methods of obtaining such antibodies and use of such antibodies.

Human MGMT is an important DNA repair enzyme which can transfer alkyl groups from $O^6$-alkylguanine and $O^4$-alkylthymine residues in DNA to a cysteine residue (Cys 167) at the active site of the enzyme. Such alkylated nucleotide residues, which can give rise to transition mutations in DNA sequences by virtue of their miscoding behaviour, can be produced by carcinogenic alkylating agents such as N-alkylnitrosoureas, e.g. N-methylnitrosourea (NMU) and N-ethylnitrosourea (NEU), and N,N-dialkylnitrosamines.

Various human genes associated with tumour formation have been found to carry point mutations, for example ras, p53 and ERCC-3. These mutations are widely believed to be crucial in the activation (oncogenes) or suppression (tumour suppressor genes) of these genes and much evidence supports point mutations arising through the action of alkylating agents on DNA being involved in the etiology of certain human cancers. Thus, it has been shown that a single dose of NMU produces mammary tumours in rats as a result of a G. C to A. T transition mutation in codon 12 of the rat H-ras oncogene. This point mutation can also be formed in vivo by substituting $O^6$-methylguanine for guanine in DNA. As $O^6$-methylguanine is one of the alkylated nucleotides formed by action of alkylating carcinogens on DNA and it can produce the G. C to A. T transition mutation, it is thought to be involved in the formation of mammary tumours in rats exposed to NMU (Zarbl et al. Nature (1985) 315, 382–385; Mitra et al. Proc. Natl. Acad. Sci. USA (1989) 86, 8650–8654).

N,N-dialkylnitrosamines are environmental alkylating agents and have also been shown to be potent tumour promoters in experimental animals. Hence, they are considered likely causative agents of human cancers through their ability to produce mutagenic DNA base adducts in vivo (Bartsch et al., Relevance of N-Nitroso compounds to Human Cancer: Exposures and Mechanisms, IARC Scientific Publication no. 84. Lyon: International Agency for Research on Cancer (1987); O'Neill, et al., Relevance To Human Cancer of N-Nitroso Compounds, Tobacco and Mycotoxins. ibid. no. 105 (1991); P. D. Lawley, in Chemical Carcinogens Vol I, Ed, C. E. Searle (ACS Monograph 182, American Chemical Society, Washington, 1984); Singer and Grunberger, Molecular Biology of Mutagens and Carcinogens (Plenum Press, New York, 1983)).

Since MGMT can specifically repair lesions in DNA produced by alkylating agents, the level of this enzyme in cells is believed to be a crucial factor in determining the sensitivity of cells towards the tumour-inducing mutagenic action of alkylating carcinogens (Lindahl et al., Annu. Rev. Biochem. (1988) 57, 133; A. E. Pegg, Cancer Res. (1990) 50 6119–6129).

A MGMT repair enzyme was first identified in bacteria. cDNAs coding for such a repair enzyme have been cloned and characterised from bacteria yeast, mice, rats and humans. MGMT thus appears to be ubiquitous protein. However, there is considerable variation in the content of MGMT between species and cell types. In *E. coli*, two proteins are known to repair $O^6$-methylguanine lesions in DNA, i.e. the ada product which is inducible and the constitutive ogt product. Bacteria carrying the ada-phenotype are sensitive to killing by alkylating agents such as NMU. Only one MGMT protein has been reported in mammals.

In addition to having implications for tumour induction, human MGMT also has implications for tumour treatment with chemotherapeutic alkylating agents such as the bifunctional chloroethylating agent 1,3-bis (2-chloroethyl)-1-nitrosurea (BCNU). The chemotherapeutic effect of such drugs depends upon formation of lethal cross-links in DNA, which may be disrupted by the suicidal repair action of MGMT. Tumour cell lines which are devoid of this enzyme (mer-or mex-tumour cell lines) are selectively sensitive to treatment with bifunctional alkylating agents such as BCNU (A. E. Pegg, Cancer Res. (1990) 50, 6119–6129; Wronski et al. Cancer Communications (1989) 5, 323–329; Brent et al. Cancer Res. (1990) 50, 58–61).

There thus is the need for reagents for assaying MGMT and/or active site alkylated MGMT in a sample or even within a single cell, e.g. by histochemical staining techniques which are known per se. Polyclonal antibodies capable of binding native human MGMT have previously been obtained (Ostrowski et al. Cancer Research (1991) 51, 3339–3344; Lee et al. Br. J. Cancer (1992) 66, 355–360). Brent et al in Cancer Research (1990) 50, 58–61 have also reported anti-MGMT monoclonal antibodies which bind human MGMT when denatured by sodium dodecyl sulphate. However, no monoclonal antibodies have previously been obtained which bind native human MGMT. Also there have been no reports of antibodies capable of discriminating between native human MGMT and this enzyme when active site alkylated. Contrary to expectations, the inventors for the present application have now found that monoclonal antibodies exhibiting such differential binding can be obtained by employing for screening an immunoprecipitation procedure with native human MGMT and an active site alkylated form of this enzyme.

Thus, in one aspect, the present invention provides an antibody capable of discriminating between native human MGMT and an active site alkylated form of this enzyme in an immunoprecipitation procedure. Preferably, such an antibody will be a monoclonal antibody.

The term "active site alkylated form of MGMT" as used herein will be understood to refer broadly to MGMT carrying at its active site an alkyl group, e.g. a $C_{1-4}$, alkyl group such at a methyl group or an ethyl group or MGMT rendered inactive by reaction of the active site cysteine residue with an alternative functionally equivalent inactivating group, e.g. a benzyl group.

In a further aspect, the present invention provides a method of selecting an antibody exhibiting the above-defined discriminating ability, which comprises determining by an immunoprecipitation procedure an antibody capable of eliciting differential precipitation of native human MGMT and an active site alkylated form of this enzyme when employed as the antigen-binding antibody.

Such a detection procedure may be carried out in conventional manner. It may, for example, comprise the steps of:

(a) contacting a first sample of a test antibody with native human MGMT, (b) separately contacting a second sample of the test antibody under the same conditions with native human MGMT after active site alkylation, (c) precipitating any antibody-antigen complex formed in steps (a) and (b), e.g. using a second antibody reagent bound to particles, e.g. agarose beads, to facilitate precipitation, and (d) detecting whether MGMT protein is precipitated.

Step (d) may, for example, comprise western blot analysis using an anti-MGMT polyclonal antibody reagent capable of binding SDS-denatured human MGMT protein. Conveniently, such a protocol may be carried out using a cell extract of cells containing human MGMT, e.g. CEM cells (human acute lymphoblast leukaemia; ATCC, USA) and a cell extract of the same cells containing MGMT in an active site alkylated form. The cell extract for step (b) may, for example, be derived from cells cultured in the presence of an agent capable of converting intracellular MGMT to an active site alkylated form. Such an agent will preferably be an alkylating nucleotide or oligonucleotide derivative, e.g. guanine having an $O^6$-alkyl group, e.g. a $C_{1-4}$ alkyl group such as a methyl group or an ethyl group, or an oligonucleotide containing such a guanine derivative. $O^6$-benzylguanine may be used.

Thus, as a preferred embodiment, the present invention provides a method of selecting an antibody according to the present invention, which comprises determining by an immunoprecipitation procedure an antibody capable of eliciting differential precipitation of native human MGMT and an active site alkylated form of this enzyme when employed as the antigen binding antibody, said procedure comprising the steps of:

(a) contacting a first sample of a test antibody with a cell extract containing native human MGMT, (b) contacting a second sample of the test antibody with a cell extract derived in the same manner as the cell extract employed in (a), but in which the MGMT has been converted to an active site alkylated form, (c) precipitating antibody-antigen complex formed in steps (a) and (b), e.g. using a second antibody reagent bound to particles to facilitate precipitation, and (d) separating any precipitated antigen by SDS-PAGE and carrying out western blot analysis as above.

According to a further aspect of the present invention, there is provided a method of preparing an antibody having discriminating ability as defined above which comprises immunising a mammal with an antigen selected from human MGMT and/or this enzyme in active site alkylated form, obtaining antibodies resulting from the said immunisation and selecting an appropriate antibody by a selection method as hereinbefore described.

For the immunisation step, purified human MGMT e.g. purified recombinant human MGMT, or a fusion protein thereof may, for example, be employed free of human MGMT in active site alkylated form. Alternatively, it may be found preferable to employ purified active site alkylated human MGMT, e.g. purified active site alkylated recombinant human MGMT, or a fusion protein thereof free of non-alkylated human MGMT. The chosen antigen will be formulated in conventional manner with an adjuvant, e.g. Freund's adjuvant. More than one immunisation may be carried out. For preparation of a polyclonal antibody reagent according to the present invention, serum will be collected from an immunised mammal for detection of antibodies having the desired discriminating ability.

A selection produce of the present invention will preferably be used to screen monoclonal antibodies of immortalised cell lines. Immortalised cell lines for this purpose may be prepared by a process which comprises the steps of (i) immunising a mammal with an antigen as above and (ii) fusing cells of lymphoid origin from the immunised mammal with cells of an immortalising cell line. In step (ii), spleen cells may, for example, be fused with tumour cells for hybridoma formation.

Immortalised cell lines producing an antibody having discriminating ability as defined above constitute a further aspect of the present invention.

In yet another aspect, the present invention provides a method of preparing a monoclonal antibody having discriminating ability as defined above which comprises culturing an immortalised cell line, e.g. a hybridoma, producing an antibody capable of selection by an appropriate immunoprecipitation procedure.

Monoclonal antibody 5H7 (Mab 5H7) obtainable from hybridoma ECACC 92112510 deposited under the Budapest Treaty at the European Collection of Animal Cell Cultures, Porton Down, Salisbury, Wiltshire SP4 OJG, U.K. on 25th Nov. 1992 represents a specific embodiment of an antibody satisfying the discriminating ability criterion for an antibody of the present invention.

Monoclonal antibody 3C7 (Mab 3C7) obtainable from hybridoma ECACC 93112514 deposited under the Budapest Treaty at the European Collection of Animal Cell Cultures, U.K. on 25th Nov. 1993 is another monoclonal antibody satisfying the discriminating ability criterion for an antibody of the present invention.

Mab 5H7 and Mab 3C7 have been found to have higher binding ability for active-site alkylated human MGMT than native human MGMT by immunoprecipitation assay. A selection immunoprecipitation procedure as discussed above may be applied to Mab 5H7 or Mab 3C7 such that only active site alkylated MGMT is detected (see section (x) of the Example and FIG. 9).

The present invention provides Mab 5H7 and antibodies which block antigen-binding of Mab 5H7. Thus, an antibody which recognises the same epitope as Mab 5H7 will competitively inhibit binding of Mab 5H7 and exhibit the same binding specifity.

The present invention also provides Mab 3C7 and antibodies which block antigen-binding of Mab 3C7.

Fragments of antibodies according to the invention may be obtained which retain their antigen binding activity, such as F(ab') and F(ab$_2$)' fragments. In addition, monoclonal antibodies according to the invention may be analyzed (e.g. by DNA sequence analysis of the genes expressing such antibodies) and humanized antibodies with complementarity determining regions which are substantially of an antibody according to the invention may be made, for example in accordance with the methods disclosed in EP-A-0239400 (Winter). Reference herein to an antibody according to the invention will be understood to include such fragments and variants.

An antibody according to the invention may be labelled with any detectable label known in the art. This may include for example an enzyme, a fluorescent label, a chemical label or a radiochemical label. The enzyme may be horse radish peroxidase; the chemical label may be biotin; and the radiochemical label may be $^{125}$I. These labels are given by way of example only.

Antibodies according to the invention have a variety of applications. They may, for example, be employed in fractionation of a sample to enrich for one of human MGMT and active site alkylated MGMT. The present invention also provides a method of determining the presence of human MGMT and/or active site alkylated MGMT in a sample which comprises contacting the sample with an antibody of the invention and detecting whether any antibody is bound.

The sample for such an assay may be an immobilised cell, or a section of such a cell, eg a histological sample. The sample may also be for example a biopsy sample of human tissue, which has been treated to make available the proteins in such a sample for immunological analysis.

Particularly preferred are methods of the present invention whereby one of human MGMT and active site alkylated forms of this enzyme may be separately detected. Mab 5H7 or an antibody which blocks antigen binding of Mab 5H7, may, for example, enable specific detection of an active site alkylated derivative of MGMT by an immunoprecipitation procedure employing Western analysis as hereinbefore described (see Example section (x) and FIG. 9). Mab 3C7 or an antibody which blocks antigen binding of Mab 3C7 may be similarly employed.

Assay methods of the present invention for detection of human MGMT and/or active site alkylated MGMT have many applications in the field of tumour diagnosis, and treatment, including diagnosis and treatment of solid tumours e.g. brain tumours. Such a method may, for example, find application in predicting malignancy potential. Such a method may be especially useful in identifying tumour cells responsive to treatment with chemotherapeutic alkylating drugs such BCNU, since the level of MGMT contributes towards the repair of DNA damaged by such treatment.

The reagents needed to perform the above methods according to the invention can conveniently be packaged into a kit. Thus, the invention provides a kit comprising an antibody according to the invention in a suitable container for storage and transport. The kit may comprise an antibody according to the invention coated upon a solid support, e.g. the walls of a micro-titre plate. The antibody may be labelled as described above. The kit may additionally comprise MGMT, active-site alkylated MGMT or a peptide fragment thereof for use in competitive assay of MGMT and/or active site alkylated MGMT. The kit may contain additional antibodies against MGMT.

In a further aspect of the invention, there is provided a method of converting MGMT to active site alkylated MGMT by bringing MGMT into contact with an alkylated oligonucleotide of from 8 to 20 nucleotides, said oligonucleotide containing an $O^6$-alkylguanine or $O^4$-alkylthymine group. An oligonucleotide for this purpose may be a methylated or ethylated oligonucleotide, preferably a methylated oligonucleotide with a substantially centrally located CmeG dinucleotide. For example, the oligonucleotide may be of the sequence: TATACmeGTATA Sequence ID NO:1.

The following Example illustrates the invention with reference to the accompanying drawings:

BRIEF DESCRIPTION OF THE DRAWINGS

FIG. 3. Specificity of affinity purified polyclonal antibodies by Western blotting analysis. Labelled lanes: 10 ng, 20 ng, 40 ng represent the amount of purified MGMT loaded, MRC5.SV40 transformed (mer-), Hela-mer+, Colo-320 and Hela-CCL2B represent 200 μg of total crude cell extract from the cell lines loaded. The polyclonal antibodies were used at 3 μg/ml and ECL was for 2 mins.

FIGS. 4A and 4B. Specificity of Protein-G sepharose purified clone 5H7 mouse antibody by Western blot analysis (B); Comparative SDS-PAGE Coomassie blue-stained gel (A). Lane 1=100 ng of purified MGMT, 2=300 ng of purified GSTMGMT, 3=reaction mixture containing 800 ng of GST-MGMT cleaved by Bovine thrombin (extra bands on the Coomassie blue staining are from the Bovine thrombin and GST). 4=2000 ng of the AA54 purified ada protein, M=molecular weight marker. 5H7 antibody was used at 3 μg/ml and ECL was for 15 mins.

EXAMPLE

Materials and Methods (i) Chemicals

Figure 1:
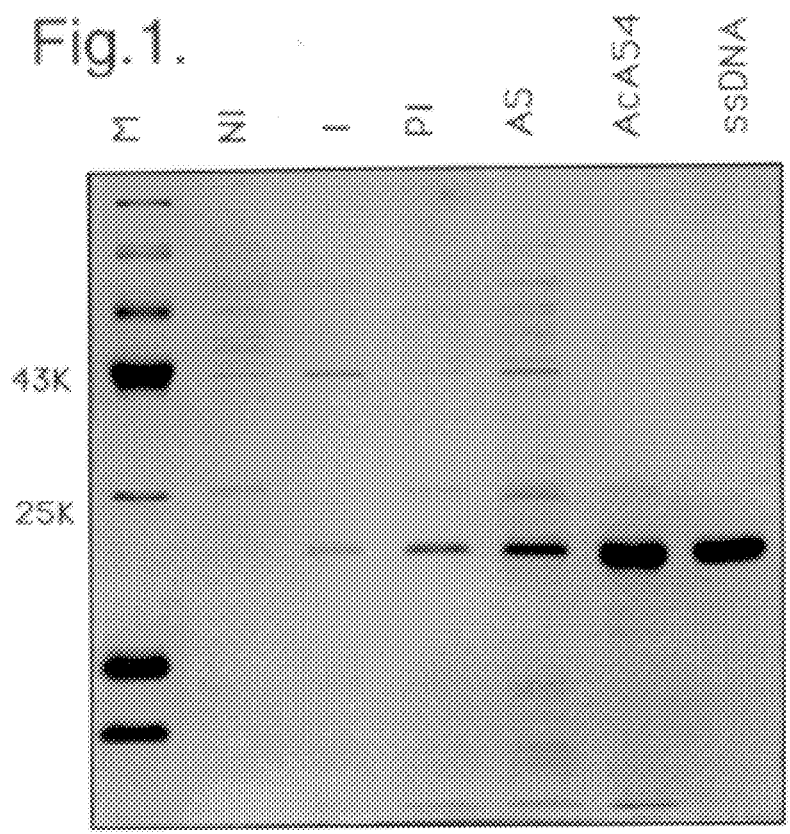
FIG. 1. Purification of expressed human MGMT. Labelled lanes: NI=non induced, I=IPTG induced, PI=supernatant of polyimine precipitation, AS=ammonium sulphate precipitation, AcA54=AcA54 gel filtration, ss DNA=single stranded calf thymus DNA linked to cellulose, M=molecular weight markers. Samples I and NI are of equal protein concentration.

The following chemicals were purchased from the respective sources and used according to the protocols supplied by the manufacturers where applicable: goat anti-rabbit IgG-HRPO, goat anti-rabbit IgG-TRITC, bovine thrombin, calf thymus single-stranded DNA cellulose, and Lowry reagents from Sigma Chemical Co. (USA); goat anti-mouse IgG-HRPO and ELISA kits from Hyclone; sheep anti-mouse IgG-FITC from Boehringer Manneheim (Manneheim, Germany); CNBr-activated Sepharose, Protein G-Sepharose, and GSH-Sepharose from Pharmacia (Sweden); ECL reagents and antibody subisotyping kit from Amersham (United Kingdom); 96-well Maxisorb immunoplate from NUNC (France); and AcA54 gel filtration matrix from IBF (France).

(ii) Cloning, Expression. and Purification of Human MGMT and GSTMGMT
(Fusion Protein of Glutathione-S-transferase to N-Terminus of MGMT)

(a) Cloning. mRNA from CEM cells (human acute lymphoblast leukaemia; ATCC, USA) was prepared by phenol extraction using standard techniques and oligo-dT cellulose. The cDNA was obtained by reverse transcription (AMV; Boehringer Mannheim, Germany) of the mRNA using oligo-dT17. The primer sequences used for PCR were obtained from the published cDNA sequence (Tano et al, Proc. Nat. Acad. Sci., USA (1990)87, 686–690). Two sets of primers were used: (a) 5'-phosphorylated 5'- pGGAAAAATGGACAAG-GATTGTGAAATGAAACGC Sequence ID No. 2 and 5'- pATACATACTCAGTTTCGGCCAGCAGGCGG Sequence ID No. 3 for cloning into pET3b (Studier et a Methods Enzymol (1990) 185: 60–88) and (b) 5'-CGACGTGGATCCATGGACAAGGATTGTGAA ATGAAACGC Sequence ID No. 4 and 5'-CCTGACGAATTCTCAGTTCGGCCAGCAGGC GG Sequence ID No. 5 for the pGEX2 vector (Pharmacia, Sweden). The PCR (kit from Perkin Elmer and Cetus, USA) conditions were as follows: 100-$\mu$l reaction mixture containing 5% of the mRNA (10 $\mu$g) reverse transcribed with oligo-T17;0.01 absorbance at 260 nm of each primer; deoxyribonucleoside triphosphates and the buffer as described by the manufacturer; and 30 cycles of 60 s at 55° C., 90 s at 72° C., and 30 s at 92° C. The PCR products were then purified on a 1% agarose gel. The purified PCR product from the second set of primers was digested with EcoRI and BamHI. The vectors pET3b (i.e., Frame 2) and pGEX2 were purified on 1% agarose gel after the following treatments: for pET3b, (a) BamHI; (b) alkaline phosphatase (CIP; Pharmacia, Sweden); and (c) T4 DNA polymerase; and for pGEX2, BamHI and EcoRI double digestion. The ligation of the inserts to the treated vectors was carried out using T4 DNA ligase at 14° C. for 12 hrs.

(b) Expression and Purification. The above ligation products were then transformed into JM109 (DE3) (Promega, USA) and plated out onto agar-LB plates containing ampicillin (40 $\mu$g/ml). Clones were picked and grown in LB (with ampicillin, 40 $\mu$g/ml) to a cell density of 0.6 to 0.8 absorbance at 600 nm. IPTG (2 mM for pET3b and 0.2 mM for pGEX2; BRL, USA) was added and the cultures were left shaking at 37° C. for 5 hrs. The bacteria were pelleted at 4000 rpm for 10 mins at 4° C. The pellets were then resuspended in Tris-HCI buffer (50 mM, pH 8.0, 2 nM EDTA and 10 mM DTT) and sonicated (6 ×10s). After addition of PSMF (20 $\mu$g/ml;

BRL, USA), the sonicated solutions were then spun at 15,000 rpm for 20 mins at 4° C. The supernatants were then assayed for the repair activity with 32pCGCmeGCG as described previously (Graves et al, Carcinogenesis (Lond) (1989) 10, 661–666).

The protocols for the large-scale preparation of MGMT and GSTMGMT were essentially as described in the literature (Bhattacharyya et al, Nucleic Acids Res. (1988) 16, 6397–6410). GSTMGMT required two cycles of AcA54 and single-stranded DNA chromatography. The 13.5% SDS-PAGE gels showing the progress of each step of purification are shown in FIGS. 1 (MGMT) and 2 (GSTMGMT).

The plasmids containing the inserts were sequenced, and a point mutation from C to T was observed at the first base of codon 84. This results in the change of leucine to phenylalanine. It is uncertain whether this mutation originated from the cell line or PCR. The purified MGMT (25 $\mu$g) was covalently linked to a DITC membrane for protein sequencing (using Prosequencer 6600; Millipore, USA). The first 25 amino acid residues obtained were exactly as the published data (Tano et al. Proc. Natl. Acad. Sci. USA (1990) 87, 686–690). No extra amino acid was introduced to the N-terminus of the cloned protein. The specificities of the two proteins, 44,000 pm/mg for MGMT and 20,500 pm/mg for GSTMGMT, were determined using an oligomer (32pTATACmeGTATA) at a known concentration and protein measurement by Bradford (using bovine serum albumin as standard; reagents from Bio-Rad, USA).

(iii) Western Blotting

SDS-PAGE (13.5%) gels were performed using a Bio-Rad (USA) miniprotein setup. Gels were then electroblotted (4 hrs, 50 mA/gel using Sartoblot II-S; Sartorius, Germany) to nitrocellulose (S&S, Germany). The filters were blocked overnight at 44° C. with a saturated solution of ovalbumin in TBS buffer [20 mm Tris HCI (pH8):0.9% NaCl solution]. The filters were then incubated with antibodies (3 $\mu$g/ml in TBS-TW20, i.e., TBS buffer with 0.05% Tween 20) for 1 hr with polyclonal antibodies and 2 hrs with monoclonal antibody at 37° C. After three 5-mins washes with TBS-TW20, the membranes were incubated with secondary antibodies: anti-rabbit HRPO-anti-IgGs for polyclonal (30 mins) and anti-mouse HRPO-anti-IgGs (120 mins) for monoclonal at 37° C. The filters were then washed as above before being visualized by ECL using the protocol as described by the manufacturer.

(iv) Cell Culture

Hela CC12B (from ATCC, USA), Hela.mer-, and Hela.mer+(from Dr. Peter Karran, ICRF, South Mimms, United Kingdom) cells were all cultured in minimal essential medium supplemented with sodium pyruvate, nonessential amino acids, L-glutamine. sodium bicarbonate, penicillin-streptomycin, and 10% fetal bovine serum (Gibco, Grand Island, N.Y.). Colo-320 HSR (from ATCC, USA) cells were cultured in RPMI 1640 and supplemented as above. MRC5 (SV40 transformed, mer-; from Dr. Peter Karran) cells were cultured in Eagle's Basal Medium and supplemented as above.

(v) Preparation of Total Cell Extracts

All cell extract preparations were carried out at 4° C. Trypsinized cells from monolayer cultures were pelleted (1100 rpm for 10 mins at 4° C.) and washed once with Hanks' balanced salt solution. Buffer [50 mM Tris(pH8.0): lmM EDTA:5 mM DTT ] in twice the packed cell volume was added to resuspend the cell pellets. The suspension was then frozen at −80° C. for 10 mins before sonification (3 times for 10 s; Heat System's Microson, USA). After addition of PMSF (25 $\mu$g/ml of cell suspension), the suspension was spun at 10,000 rpm for 10 mins. The supernatants were then aliquoted and stored at −80° C.

(vi) Rabbit Polyclonal Antibodies

Polyclonal antibodies were raised by giving rabbits (*Orvctolagus cuniculus*) injections of the cloned human MGMT (100 $\mu$g/animal, Fraction 8 of the final single-stranded DNA column, as shown in FIG. 1) every 4 weeks. High-affinity polyclonal antibodies (by Western blotting analysis of the serum) were obtained from the seventh boost.

The serum was the further purified with the cloned MGMT (1 mg coupled to 200-μl packed gel volume, CNBr-activated Sepharose) affinity column. Before eluting with glycine (Harlow and Lane, Antibodies: A Laboratory Manual, Cold Spring Harbor, N.Y. 1988), the antibody-antigen matrix was washed with 1 M NaCl. These affinity-purified antibodies were used for all experiments. The specificity of these antibodies on crude cell extracts is shown in FIG. 3.

(vii) Mouse Monoclonal Antibody

The protocols for immunization and fusion were followed exactly as described by Harlow and Lane (Antibodies. A Laboratory Manual. Cold Spring Harbor Laboratory, 1988). BALB/c mice were given injections of active-site methylated human MGMT [100 μl containing 120 μg of MGMT from Fraction 8 of the single-stranded DNA column were added to a solution (30 μl) containing 4 absorbance at 260 nm of TATACmeGTATA Sequence ID No. 1 in buffer consisting of 50 mM Tris-HCl (pH 8.0), 1 mM EDTA, and 5 mM DTT; the solution was then incubated at 37° C. for 30 mins before mixing with Freund's adjuvant (1:1) for injection into 4 mice]. Mouse monoclonals were produced by fusing spleen cells from immunized mice (after 9 months) with NS-1 cells (ATCC, USA). The fusion cells were plated out in 18-x 96-well tissue culture plates. The clones were screened by ELISA using 96-well immunoplates coated with either active site-methylated or -unmethylated antigen. Positive clones were further screened by Western blotting as in (iii) above and by immunoprecipitation assay as in (x) below.

The clone 5H7, producing a monoclonal antibody sub-isotyped to be IgGl, was grown in 2 litres. The monoclonal antibody was purified by Protein G. The Western blotting analysis is shown in FIG. 4, Lane 3 is GSTMGMT (10 μl from Fraction 8) cleaved with bovine thrombin (10 ;1, containing 1 μl of thrombin in PBS) at 4° C. for 2h. The extra bands observed are from thrombin, and the intense band above MGMT is the GST. Lane 4 is the *E. coli* M, 39,000 ada protein (from bacterial stock pBar2; a gift from Dr. B. Sedgwick and Dr. T. Lindahl, ICRF, South Mimms).

Monoclonal antibody 3C7 was obtained by the same procedure as monoclonal antibody 5H7.

(viii) Cell Staining

Figure 5:
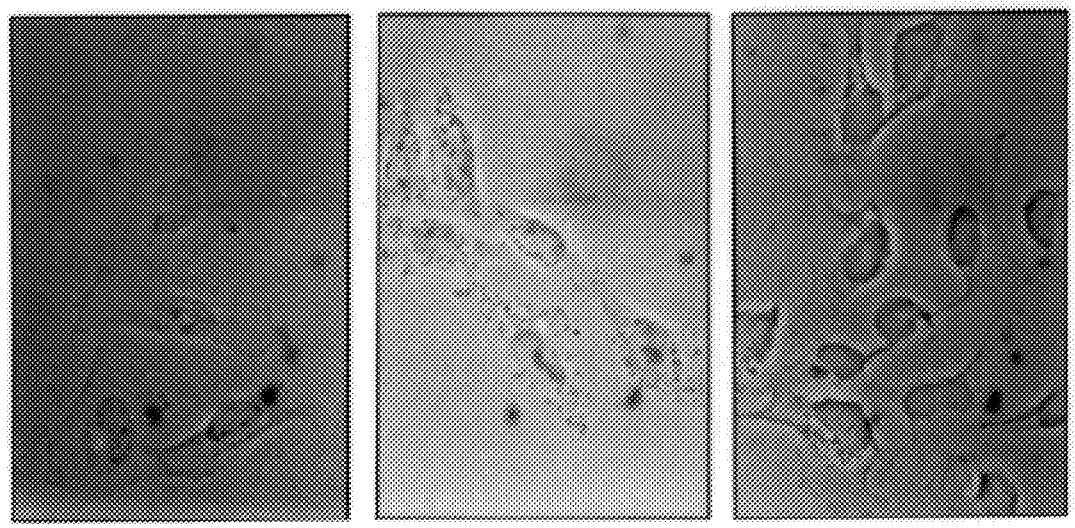
FIG. 5. Cytoimmunofluorescence staining of Hela.CCL2B (mer+), Hela,mer-and MRC5.SV40 transformed (mer-) by affinity purified rabbit polyclonal antibodies. The antibodies were used at 25 μg/400 μl. The top panel is the bright and the bottom is the fluorescence field.
Figure 5:
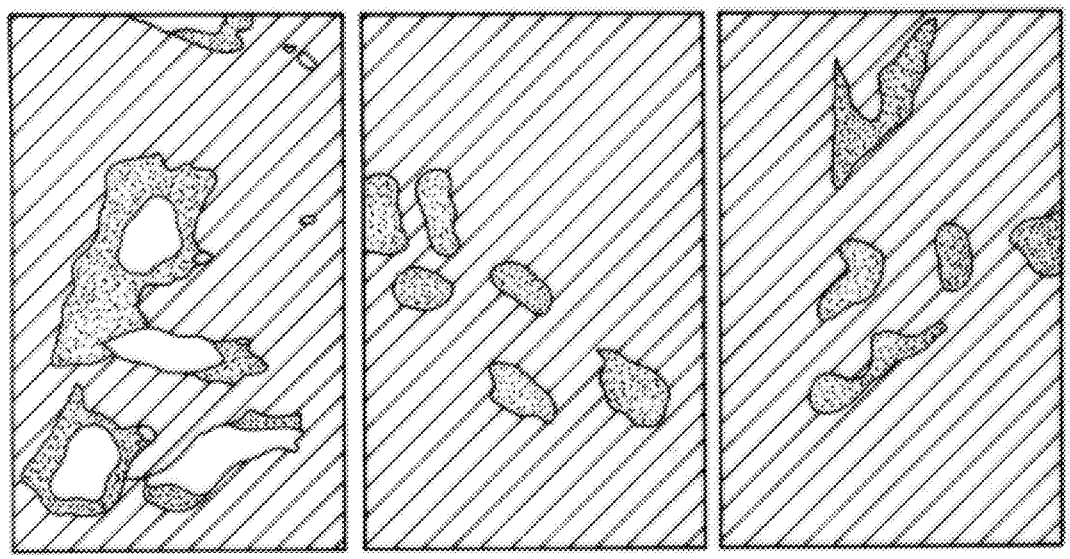

Monolayer cells were grown on slides for 2 days. After fixing with paraformaldehyde (10 mins, 4% in PBS; Fluka. Germany), the slides were washed with PBS for 10 mins. Cells on the slides were permeabilized with 0.1% Triton X-100/PBS solution for 10 mins. The slides were soaked in a solution containing 10% lamb serum (for monoclonal) or 10% goat serum (for polyclonal) in 0.1% Triton X-100/PBS for 10 mins. Primary polyclonal or monoclonal antibodies (20 to 40 μg in 400 μl of 1% Triton X-100/PBS per slide) were then added onto the slides. The slides were incubated in a moist chamber overnight at 4° C. The primary antibody-treated slides were then washed twice (10 mins. each) with 0.1% Triton X-100/PBS before blocking with 10% goat or lamb serum in 0.1% Triton X-100/PBS for 10 mins. Secondary antibody (1:32 or 1:30 diluted in 1% Triton X- 30 100/PBS, for anti-rabbit TRITC for polyclonal and anti-mouse FITC for monoclonal, respectively) was added, and the slides were incubated in the dark at room temperature for 1 hr. The slides were then washed three times (5 mins each) with PBS and mounted with coverslips using Permafluor (Lipshaw, Immunon, Pittsburgh, Pa.). After overnight polymerization in the dark at room temperature, the slides were examined under a fluorescence microscope (Axioplan POI fixed with a MC100 camera; Zeiss, Germany) using blue excitation for FITC (mouse monoclonal) and green excitation for TRITC (rabbit polyclonal). The cytoimmunofluorescence staining on different cell lines is shown in FIG. 5 (rabbit polyclonal) and FIG. 6 (clone 5H7 mouse antibodies).

(ix) Depletion of Clone 5H7 Mouse Antibodies by GST-MGMT-GSH-Sepharose

Fusion protein, GST-MGMT (8.2 nmol, from Fraction 8 of the second single-stranded DNA column), was immobilized by incubation for 1 h at 4° C. with either 30 μl, 120 μl or 240 μl of GSH-Sepharose (50% suspension PBS) pre-washed twice with PBS. The supernatant containing the unbound fusion protein was removed, and the beads were washed three times with PBS (3×1 ml, with 0.5 mM DTT). After the last wash, the beads were then resuspended in PBS (made to a 50% suspension). The 3 samples were then incubated with an equal amount of antibody from 5H7 (100 μl of 3 μg/μl) for 2 hrs at 4° C. with shaking. The suspension was then pelleted at 2000 rpm, and the supernatant containing the residual antibodies was analyzed by SDS-PAGE and Western blotting (Fig. 7) and cell staining with Hela-CC12B (FIG. 8).

(x) lmmunoprecipitation of MGMT and active-site alkylated MGMT from CEM cell extracts by Mab 5H7 a. Cell extracts

CEM cells (human acute lymphoblast leukaemia; ATCC, USA) were cultured 1:1 of MEM and RPMI in 10% of FBS with supplements. Cells at log phase, 400 ml, were aliquoted into two flasks (200 ml ). One flask was treated with 50 ml of normal medium as control and the other was treated with 50 ml of medium containing 100 μM of $O^6$-benzylguanine for generation of active-site alkylated MGMT. Cells were then grown at 37° C. for 1 hr and harvested by spinning at 1000 rpm. The cell pellets were then frozen at −80° C. and cell extracts were then prepared by resuspending in buffer A (200 μl of 50 mM Tris pH 8, ImM EDTA, 10 μM PMSF and 0.3M NaCl) and sonicated. The sonicated extracts were then spun at 50,000 rpm for 30 mins at 4° C. The supernatants were then aliquoted and stored at −80° C.

Treatment of cells with alkylating carcinogens can produce some DNA lesions other than $O^6$-alkylguanine. The comparison of the abilities of monoclonal antibodies to immunoprecipitate MGMT protein from cell extracts which have been obtained from $O^6$-benzylguanine treated and non-treated CEM cells is therefore informative to assess their specificities towards active MGMT and active site alkylated MGMT.

b. Immunoprecipitation

400 μg of the above cell extracts were diluted with buffer A to 200 μl and 1 μg of Mab 5H7 or Mab 3C7 was added (protein G, Pharmacia, purified). The reaction mixtures were then shaken for 1 hr at 4° C. 20 μl of anti-mouse Fc linked to agarose was then added to each reaction mixture. After further shaking at 4° C. for 30 mins, the reaction mixtures were then spun at 1000 rpm. The supernatants were then removed. After washing with 3×300 μl of buffer A, 10 μl of 4 ×Lamenli loading buffer was added to the agarose beads and the samples were then boiled at 100° C. for 10 mins before analysis by 13.5% SDS/PAGE. After transfer to nitrocellulose, the MGMT/alkylated MGMT was visualised by Western analysis using affinity purified polyclonal antibodies towards MGMT prepared as in (vi) above.

RESULTS

Source of Antigens

Figure 2:
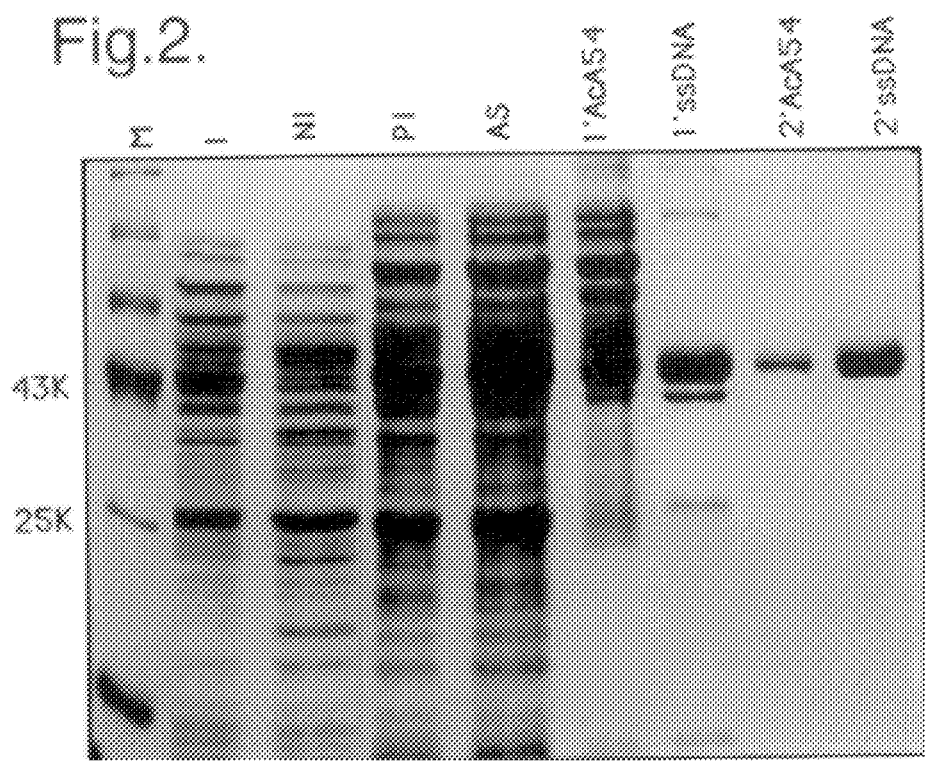
FIG. 2. Purification of the expressed fusion protein Gluthathionne-S- transferase fused to the N-terminal of human MGMT (GSTMGMT). Labelled lanes: NI non induced, I=IPTG induced. PI=supernatant of polyimine precipitation, AS=ammonium sulphate precipitation, AcA54=AcA54 gel filtration, ssDNA=single stranded calf thymus DNA linked to cellulose, M=molecular weight markers. Samples I and NI are of equal protein concentration.

The human MGMT and the glutathione-S-transferase fusion protein (GSTMGMT) were expressed in milligram quantities and purified to high specific activity from *E. coli* (FIGS. 1 and 2). This enabled us to raise antibodies under different conditions. We immunized with the native antigens with the aim of producing antibodies to exposed epitopes of the antigen for cell staining and immunoprecipitation.

Active site methylated MGMT was used as the antigen for the monoclonal work to favour production of monoclonal antibodies having preference for the methylated protein.

Specificity of Rabbit Polyclonal Antibodies

FIG. 3 summarizes Western analysis of the total cell extracts of the following cell lines: MRC5.SV40 transformed (mer-); Hela.mer+; Hela. CC12B (mer+; and Colo-320 HSR (mer-). The most intense MGMT band observed is from the Hela.mer+. this is about 4 ng/200 μg or 0.002% of the total crude cellular protein. The amount of MGMT in Hela.CCL2B is 3 to 4 times less than the Hel.mer+(by comparison of different ECL exposures). this polyclonal antibody detects the MGMT in normal cels as a major band in the crude cell extracts, indicating that there is little cross-reactivity. The faint bands present at a molecular weight of 21,000 in the deficient cell lines may suggest MRC5. SV40-transformed (mer-) and Colo. 320 HSRs do have a low level of the repair enzyme.

Binding Ability of Mab 5H7 by Eliza screening and Western Blot Analysis

By Eliza screening or Western blot analysis. Mab 5H7 was observed to bind both active site methylated MGMT and non-methylated MGMT (denatured or nondenatured) (see FIG. 7). However. this antibody is not as sensitive as the polyclonal preparation (minimum detection requires 30 to 40 ng; results not shown) by Western blotting analysis. Therefore, it cannot be used to duplicate the Western analysis of the crude cell extracts shown in FIG. 3. However, by using a higher concentration of the MGMT, GSTMGMT, and ada protein, it is possible to assess the nonspecific signal produced by the monoclonal. It is apparent from FIG. 4 that the antibody does not cross-react with the M, 39,000 ada protein (Lane 5) or the GST (Lane 3, M,25,000 band).

Immunoprecipitation of MGMT and active-site alkvlated MGMT from cell extracts by Mab 5H7 and Mab 3C7

Figure 9:
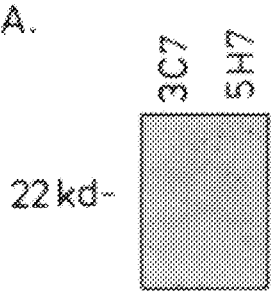
FIGS. 9A and 9B. Western blot analysis of immunoprecipitation of MGMT and MGMT in an active site alkylated form from CEM cell extracts by monoclonal antibody 5H7 and monoclonal antibody 3C7.A. Cell extract from cells not treated with alkylating nucleotide B. Cell extract from cells treated with $O^6$-benzylguanine.
Figure 9:
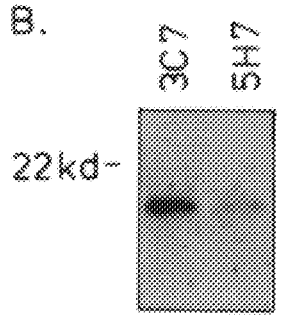

FIG. 9 shows that in the immunoprecipitation procedure as described above in (x), neither Mab 5H7 nor Mab 3C7 effectively immunoprecipitates MGMT. Substantially more MGMT protein is observed by Western Analysis when using cell extracts from cells treated with $O^6$-benzylguanine.

Cytoimmunofluorescence Staining

One problem with the cytoimmunostaining technique is assessing the specificity of any positive staining obtained. Two approaches were used to address this: (a) use of cell lines known to express MGMT at different levels and (b) competition of the signal by the pure antigen. FIG. 5 shows cytoimmunofluorescence staining of Hela-CC12B (mer+), Hela.mer-, and MRC5.SV40-transformed (mer-) cells using the affinity-purified rabbit polyclonal antibodies. The observed intensity of fluorescence varies significantly among the cell lines and correlates well with Western analysis of corresponding cell extracts (FIG. 3). This confirms that the signal observed is only due to binding of the antibodies to the repair protein in fixed cells. The staining in the MRC5. SV40-transformed (mer-) cells probably represents the lower limit of detection by this method, being 4 to 5 times above the background (i.e. without primary antibody; data not shown). These data show the repair protein to be mainly located in the nucleus of the Hela.CCL2B and the Hela.mer-cells. However, in the MRC5.SV40-transformed (mer-) cells, a certain proportion showed general staining.

Figure 6:
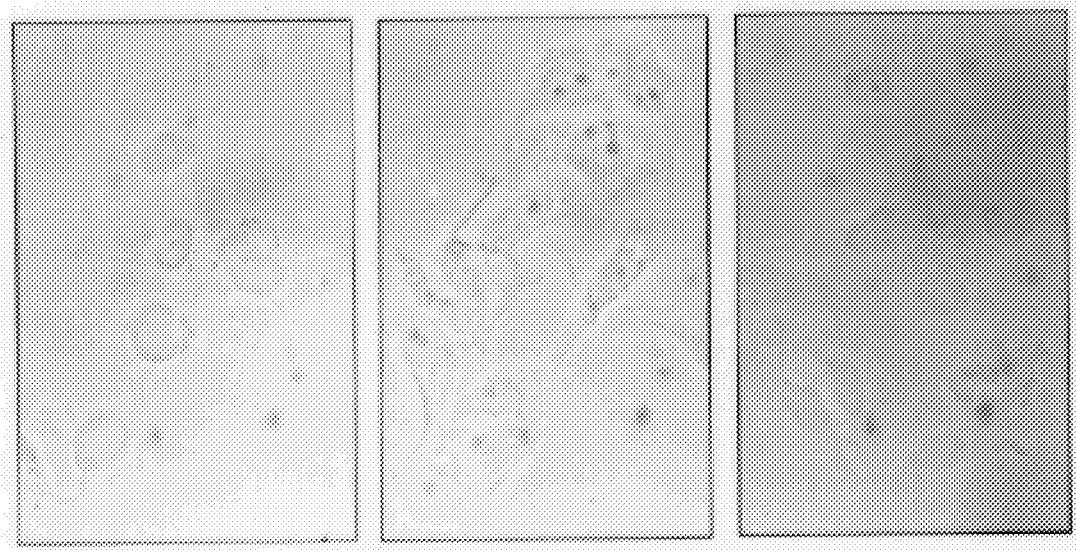
FIG. 6. Cytoimmunofluorescence staining of HEla.CCL2B (mer+), Hela.mer-and MRC5.SV40 transformed (mer-) by Protein-G Sepharose purified clone 5H7 mouse antibody. the antibody was used at 30 μg/400 μg. Top panel is the bright and the bottom is the fluorescence field.
Figure 6:
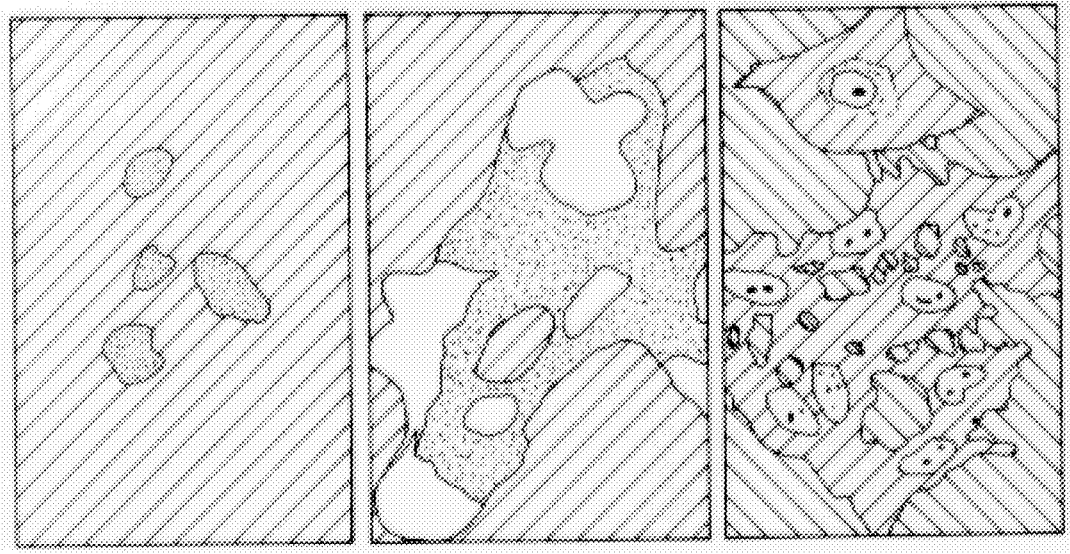
Figure 6:
Figure 6:
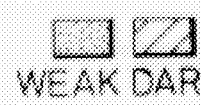
Figure 6:
Figure 6:
Figure 6:
Figure 6:

FIG. 6 shows immunofluorescent staining of the cells using monoclonal 5H7 antibody. The fluorescent signal is clearly more refined than the polyclonal staining. MGMT is observed throughout the nucleus of the Hela.CCL2B cells, but the nucleolus is not stained. The pattern of the fluorescence is similar in the 3 cell lines, with decreasing intensity from Hel.CCL2B (mer+) to Hela.mer-to MRC5-SV40-transformed (mer-) cells. As SDS-PAGE gel analysis of the Protein G-Sepharose-purified clone 5H7 mouse antibody shows various proteins in addition to the monoclonal antibody bands, final confirmation is required to show that only the specific component which binds to the pure antigen is responsible for the fluorescence observed in the nucleus.

Figure 7:
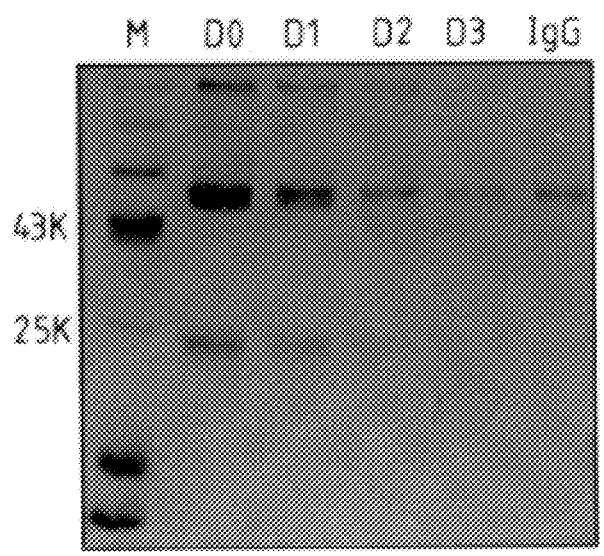
FIGS. 7A and 7B. Depletion of clone 5H7 mouse antibody by immobilised GSTMGMT-GSH-sepharose with analysis by SDS-PAGE and Western analysis. D0=no depletion; D1, D2 and D3 represent depletion of 300 μg/100 μl of 5H7 antibody by 30 μl, 120 μl, and 240 μl of saturated GSTMGMT-GST.sepharose respectively. Lanes in the Coomassie Blue stained SDS PAGE gel contain 3 μl of D0, D1, D2 and D3; IGg-bovine IGg. Lanes in Western analysis contain 80 ng of MGMT (M) active site methylated with 2 xdecamer TATACmeGTATA Sequence ID No:1; N=MGMT not methylated. Equal volume of the samples D0(3 μg/ml), D1, D2 and D3 were used for the Western analysis.
Figure 7:
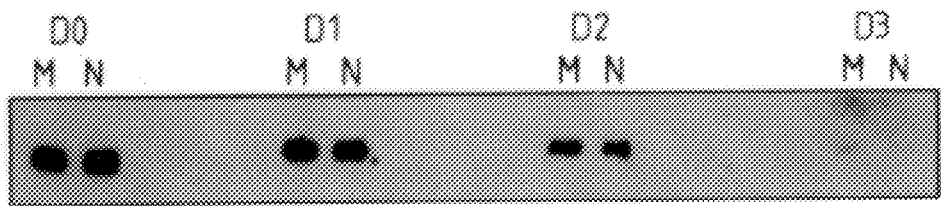
Figure 8:
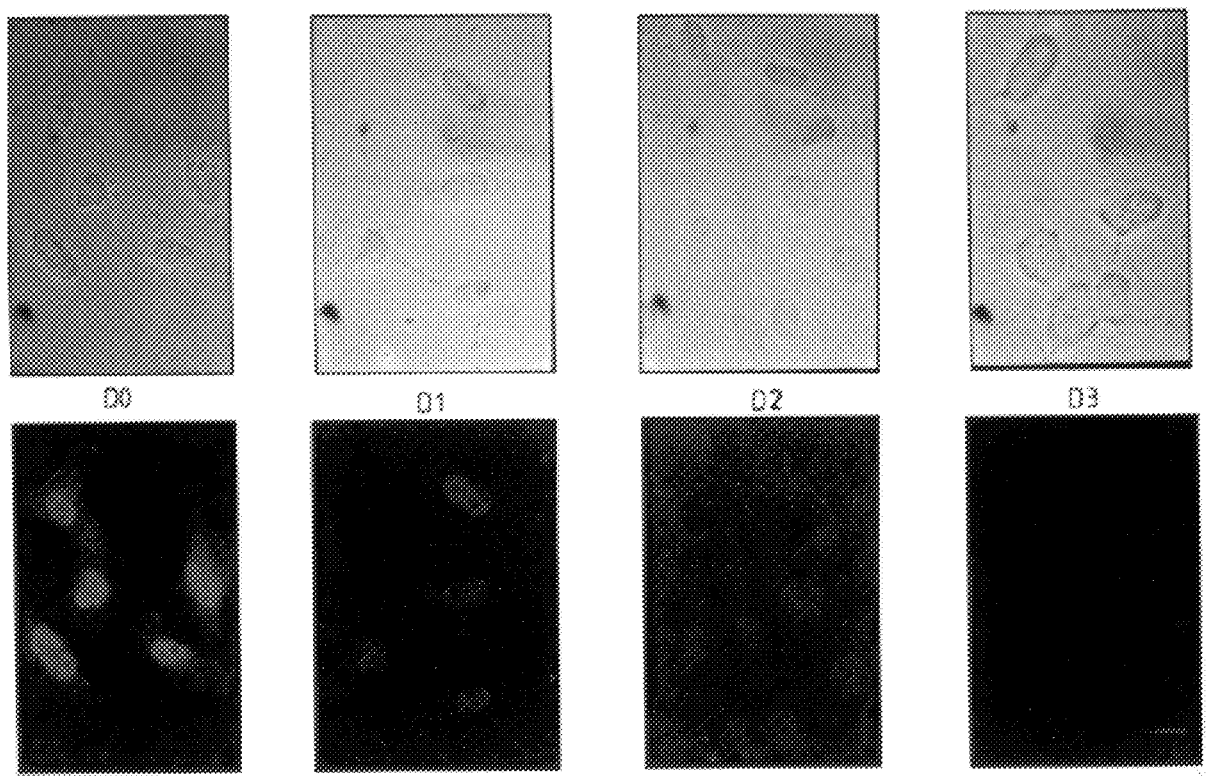
FIG. 8. Depletion of clone 5H7 mouse antibody by immobilised GSTMGMT-GSH-sepharose. Analysis by cytoimmunofluorescence staining of Hela.CCL2B (mer+). D0=no depletion, D1, D2 and D3 represent depletion of 300 μg/100 μl of 5H7 antibody by 30 μl,120 μl and 240 μl of saturated GSTMGMT-GSH-sepharose. Equal volumes of the samples D0(30 μg/400 μl), D1, D2 and D3 were used for cell staining. The top panel is the bright and the bottom is the fluorescence field.

FIG. 7 (SDS-PAGE Coomassie blue-stained gel and Western blotting) and 8 (the corresponding staining of Hela-CC12B) summarize the depletion of the 5H7 antibodies by an increasing amount of GSH-Sepharose saturated with GSTMGMT, (GSTMGMT-GSH-Sepharose). In FIG. 7, the Coomassie blue staining of the $M_r$ 52,000 heavy chain and the $M_r$ 23,500 light chain decreases from D1 to D2 to D3 (which represents the depletion of the 5H7 antibodies by 30, 120 and 240 μl of GSTMGMT-GSH-Sepharose). The corresponding Western analysis and the fluorescence in FIG. 8 all decrease accordingly. In FIG. 7, the extra bands (i.e., above the heavy chain in the Coomassie-stained gel) which cannot be depleted do not contribute to the fluorescence observed. These data undoubtedly show that only the 5H7 antibodies are responsible for the fluorescence observed in the nucleus of the above 3 cell lines studied.

CONCLUSIONS

1. The Western analysis of the total cellular extracts from various cell lines using the affinity purified polyclonal antibodies (FIG. 3) established the MGMT content in these cell lines in the following order: Hela.mer+; Hela.CC12B; Colo-320HSR; and MRC5.SV40 transformed (mer-). This is in agreement with previous results. This result suggests that the polyclonal antibodies are of high specificity. As the Western analysis (FIG. 3) and immunostaining (FIG. 5) correlate well with the MGMT content in the cells studied, the fluorescence observed in the nuclei of the cells studied arises from the MGMT inside the cell. The differential staining in the mer-and the mer+ cell lines (FIG. 6) and the depletion experiments by pure GSTMGMT-GHS-Sepharose (FIGS. 7 and 8) are sufficient to establish that Mab 5H7 can also be used to locate MGMT within cells. Mab 3C7 may be substituted for Mab 5H7 for this purpose.

2. Ability of Mab 5H7 and Mab 3C7 to discriminate between native MGMT and this enzyme when active site alkylated can be observed by assessment of binding of the monoclonal antibodies to these two enzyme forms by immunoprecipitation. The same methodology may be usefully employed to select other antibodies having discriminating ability between native and active-site alkylated MGMT.

We claim:

1. The monoclonal antibody 3C7 obtainable from hybridoma ECACC 93112514 and antibodies which recognize the same epitope as monoclonal antibody 3C7 and competitively block binding of monoclonal antibody 3C7 to active site alkylated human $O^6$-methylguanine-DNA-methyltransferase (MGMT).

2. A monoclonal antibody as claimed in claim 1; which recognizes the same epitope as monoclonal antibody 3C7 and competitively blocks the binding of monoclonal antibody 3C7 obtainable from hybridoma ECACC 93112514 to active site alkylated human MGMT.

3. An antibody according to claim 1 or claim 2 labelled with a detectable label.

4. A method of preparing an antibody which recognizes the same epitope as monoclonal antibody 3C7 and competitively blocks binding of monoclonal antibody 3C7 to active site alkylated human $O^6$-methylguanine-DNA-methyltransferase (MGMT), which method comprises the steps of:

(a) immunising a mammal with human MGMT in active-site alkylated form, (b) obtaining antibodies resulting from said immunisation, and (c) selecting an antibody which recognizes the same epitope as monoclonal antibody 3C7 and competitively blocks binding of monoclonal antibody 3C7 to active site alkylated human MGMT.

5. The method of claim 4 wherein said selecting is by immunoprecipitation.

6. A method of preparing a monoclonal antibody which recognizes the same epitope as monoclonal antibody 3C7 and competitively blocks binding of monoclonal antibody 3C7 to active site alkylated human $O^6$-methylguanine-DNA-methyltransferase (MGMT), which method comprises the steps of:

(a) immunising a mammal with human MGMT in active-site alkylated form, (b) fusing cells of lymphoid origin from the immunized animal with cells of an immortalized cell line, (c) culturing the resulting fused cells, and (d) isolating a monoclonal antibody which recognizes the same epitope as monoclonal antibody 3C7 and competitively blocks binding of monoclonal antibody 3C7 to active site alkylated human MGMT.

7. An immortalized cell line which produces an antibody according to claim 1 or claim 2.

8. The immortalized cell line line of claim 7 which is hybridoma ECACC 93112514.

9. A method of determining the presence of active site alkylated MGMT in a sample which comprises contacting the sample with an antibody as claimed in claim 1 or claim 2 and detecting whether any antibody is bound.

10. A method according to claim 9 wherein the sample is an immobilized cell.

11. A method according to claim 9 or claim 10 wherein the sample is obtained from a patient with a carcinoma, either prior to or after the patient has received chemotherapy.

12. A kit comprising an antibody according to claim 1 or claim 2 in a suitable container for storage and transport.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 6
    ( D ) OTHER INFORMATION: /note= "The N at position 6 is methylG"

( x i ) SEQUENCE DESCRIPTION: SEQ ID NO: 1:

TATACNTATA                                                                                              10

( 2 ) INFORMATION FOR SEQ ID NO: 2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

GGAAAAATGG ACAAGGATTG TGAAATGAAA CGC                                                                    33

( 2 ) INFORMATION FOR SEQ ID NO: 3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

ATACATACTC AGTTTCGGCC AGCAGGCGG                                                                         29

( 2 ) INFORMATION FOR SEQ ID NO: 4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

CGACGTGGAT CCATGGACAA GGATTGTGAA ATGAAACGC                                                              39

( 2 ) INFORMATION FOR SEQ ID NO: 5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 5:

CCTGACGAAT TCTCAGTTCG GCCAGCAGGC GG                                                                     32